United States Patent [19]

Ganguly et al.

[11] 4,435,388

[45] Mar. 6, 1984

[54] TYLOSIN 20-IMINO-20-DEOXO-4"-ACYL DERIVATIVES, PHARMACEUTICAL COMPOSITIONS AND METHOD OF USE

[75] Inventors: Ashit K. Ganguly, Upper Montclair; Alan K. Mallams, West Orange;; Yi-Tsung Liu, Parsippany, all of N.J.

[73] Assignee: Schering Corporation, Kenilworth, N.J.

[21] Appl. No.: 386,834

[22] Filed: Jun. 10, 1982

[51] Int. Cl.$^3$ ..................... A61K 31/71; C07H 17/08
[52] U.S. Cl. ..................................... 424/180; 536/7.1
[58] Field of Search ........................ 424/180; 536/7.1

[56] References Cited

U.S. PATENT DOCUMENTS

| | | | |
|---|---|---|---|
| 4,268,665 | 5/1981 | Sakakibara et al. | 536/7.1 |
| 4,279,896 | 7/1981 | Ganguly et al. | 536/7.1 |

FOREIGN PATENT DOCUMENTS

| | | | |
|---|---|---|---|
| 2077730 | 12/1981 | United Kingdom | 536/7.1 |
| 2077731 | 12/1981 | United Kingdom | 536/7.1 |

OTHER PUBLICATIONS

Tsuchiya et al., "The Jour. of Antibiotics", vol. XXXV, No. 6, pp. 661-672, 1982.
Toju et al., "Drug Action and Drug Resistance in Bacteria" Univ. of Tokyo Press, Tokyo, Japan, 1971, pp. 284-287.
Derwent Abstract-Japanese Pat. #J56147-798, 3/31/80.
Derwent Abstract-European Patent #45-157, 7/24/80.

*Primary Examiner*—Johnnie R. Brown
*Attorney, Agent, or Firm*—Anita W. Magatti; Gerald S. Rosen

[57] ABSTRACT

There are disclosed 20-imino-20-deoxo-4"-acyl derivatives of the antibiotic tylosin which have higher serum levels and better absorption than the parent tylosins. Methods of preparation of the compounds are also disclosed.

45 Claims, No Drawings

TYLOSIN 20-IMINO-20-DEOXO-4"-ACYL DERIVATIVES, PHARMACEUTICAL COMPOSITIONS AND METHOD OF USE

BACKGROUND

This invention relates to a novel class of macrolide antibacterial agents. More particularly, this invention relates to antibacterial 20-imino-20-deoxo-4"-acyl derivatives of tylosin.

Tylosin and numerous acyl derivatives thereof are known in the antibiotic art. For instance, U.S. Pat. No. 4,268,665 discloses 3-, 3"- and 4"- acyl tylosin derivatives and U.S. Pat. No. 4,205,163 describes 3,- 2'- and 4"-acyl tylosin derivatives.

SUMMARY

We have now discovered that certain 20-imino-20-deoxo-4"-acyl derivatives of tylosin possess potent and broad spectrum antibacterial activity against gram-positive strains, and most advantageously, possess higher serum levels and are better absorbed than the compounds previously known in the art.

DETAILED DESCRIPTION

In its composition of matter aspect, the present invention embraces compounds of the formula:

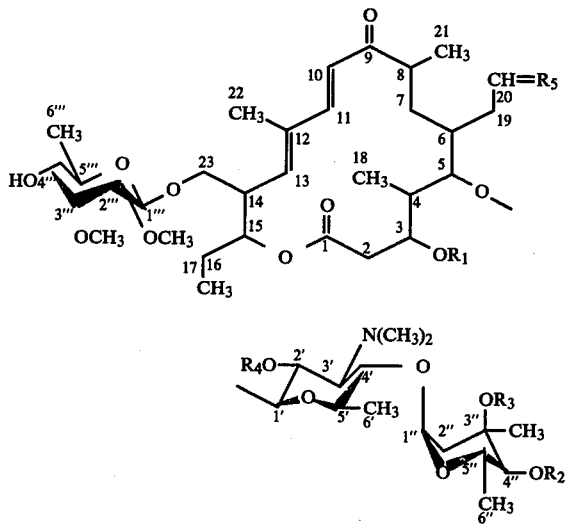

wherein
$R_1$ is hydrogen or acyl;
$R_2$ is acyl;
$R_3$ is hydrogen or acyl; or $R_2$ and $R_3$ are together a carbonyl group joining 4"- and 3"- hydroxyl groups;
$R_4$ is hydrogen or acyl;
$R_5$ is selected from the group consisting of

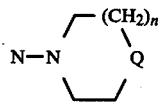

wherein
n is 0-2, and
Q is selected from the group consisting of $CH_2$, $CHR_6$, $CHR_7$, $CR_6R_7$, $NH$, $NR_6$, $O$, $S$, $SO_2$, $CHOH$, $CHOR_6$, $CHOR_7$,

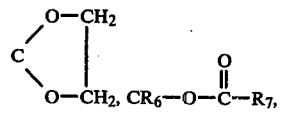

$CHCOOH$, $CHCOOR_6$, $CHCONH_2$ and $CHCONR_6R_7$, wherein $R_6$ and $R_7$ may be the same or different, each being a member of the group consisting of $(C_1-C_6)$alkyl, $(C_7-C_{10})$aralkyl and $(C_6-C_{10})$aryl including X-substituted aryl and aralkyl, wherein X is halogen, trifluoromethyl, $(C_1-C_6)$ alkoxy, or $(C_1-C_6)$ alkylcarbonyl;
N-NH-aralkyl, and

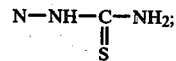

and the non-toxic pharmaceutically acceptable acid addition salts thereof.

Although no stereochemical configuration is indicated for the structure above, it is to be understood that the stereochemical configuration is identical to that of tylosin.

The term "$(C_1-C_6)$ alkyl groups" as used herein means alkyl groups with 1 to 6 carbon atoms, e.g. methyl, ethyl, propyl, butyl, pentyl, hexyl and the corresponding branched-chain isomers thereof.

The term "$(C_1-C_6)$ alkoxy groups" as used herein means alkoxy groups with 1 to 6 carbon atoms, e.g. methoxy, ethoxy, propoxy and the like.

The term "$(C_6-C_{10})$ aryl" as used herein means phenyl and phenyl substituted by one or more substituent groups selected from among halogen, where halogen includes fluoro, chloro and bromo; trifluoromethyl, alkoxy and alkylcarbonyl. Such aryl groups are, for example, 2-fluorophenyl, 2,6-dimethoxyphenyl, 3,4-dichlorophenyl and 3-bromophenyl.

The term "$(C_7-C_{10})$ aralkyl" encompasses aryl substituted lower alkyl groups, such as benzyl, phenethyl, p-fluorobenzyl, o-tolylethyl and m-chlorophenethyl.

The term "$(C_1-C_6)$ alkylcarbonyl groups" as used herein means those which contain one to five carbon atoms in the alkyl portion e.g. acetyl, propionyl, butyryl and the like.

As used herein, the term "acyl" means acyl groups derived from organic acids such as acetic, chloroacetic, propionic, butyric, iso-valeric, alkoxycarbonic, oxalic, oleic, palmitic, stearic, lauric, valeric, benzoic, cyclopropanecarboxylic, cyclohexanecarboxylic, β-cyclohexylpropionic, adamantanecarboxylic, phenylacetic, phenoxyacetic, mandelic and 2-thienylacetic acids and alkyl-, aryl- and aralkylsulfonicacids, the aryl and aralkyl acids are optionally substituted by halogen, nitro, alkoxy and the like on the aromatic moiety. Suitable esters also include hemi-esters derived from dicarboxylic acids such as succinic, maleic, fumaric, malonic and phthalic acids. Particularly preferred acyl groups are those derived from alkanoic acids of 2 to 5 carbon atoms, such as acetyl, propionyl, n-butyryl and iso-valeryl.

Particularly preferred compounds of the present invention are those wherein $R_5$ is a group of the formula

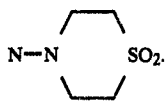

Also preferred are compounds wherein $R_1$, $R_3$ and $R_4$ are hydrogen and $R_2$ is an acyl group selected from the group consisting of acetyl, propionyl, n-butyryl and iso-valeryl, or $R_1$ is acetyl, $R_3$ and $R_4$ are hydrogen and $R_2$ is an acyl group selected from the group consisting of acetyl propionyl, n-butyryl and iso-valeryl. Other preferred compounds include those where $R_1$ and $R_3$ are hydrogen and $R_2$ and $R_4$ are acyl groups selected from the groups consisting of acetyl, propionyl, n-butyryl and iso-valeryl; those where $R_1$ and $R_4$ are hydrogen and $R_2$ and $R_3$ are independently acyl groups selected from the group consisting of acetyl, propionyl, n-butyryl and iso-valeryl; those where $R_1$ is hydrogen and $R_2$, $R_3$ and $R_4$ are independently acyl groups selected from the group consisting of acetyl, propionyl, n-butyryl, iso-valeryl; and those where $R_2$ and $R_3$ together are a bridging carbonyl group.

The compounds of the present invention are capable of forming non-toxic, pharmaceutically acceptable acid addition salts with inorganic and organic acids by virtue of the dimethylamino group at position 3'. By "non-toxic pharmaceutically acceptable acid addition salts" is meant those that do not exhibit toxic manifestations at normal therapeutic doses. Exemplary of such salts are those formed with such acids as hydrochloric, sulfuric, phosphoric, citric, acetic, propionic, tartaric, maleic, benzoic, cyclopropylcarboxylic, adamantylcarboxylic, laurylsulfonic, glucoheptonic, stearic and the like. Acid addition salts may be prepared by methods generally used in the art such as by adding a stoichiometric amount of acid to a solution of the compounds in a non-reactive organic solvent and isolating the salt by art known methods such as precipitation of the salt with a solvent wherein the salt is not appreciably soluble, e.g. diethyl ether. A non-reactive organic solvent is one which does not react with the compound, the acid or the salt.

In its process aspect, this invention embraces a method of eliciting an antibacterial response in a mammal having a bacterial infection which comprises administering to the mammal a therapeutically effective quantity of a compound as defined in formula I.

In order to elicit an antibacterial effect, the compounds of this invention may be administered orally, topically, intramuscularly or intraveneously. Administration may be effected by any of the conventional methods, i.e., by the use of tablets, capsules, suspensions, solutions, injectable creams or ointments. Each of the dosage forms can be formulated utilizing non-toxic pharmaceutically acceptable excipients conventionally known in the art. The compounds of this invention are preferably administered at from about 5 mg to about 50 mg per kg per day in single or divided doses.

The compounds of this invention are antibacterial agents exhibiting a broad spectrum of activity against gram-positive strains and having significant activity against numerous strains of Staphylococcus, Streptococcus, Bacillus and Sarcina.

The antibacterial activity of the compounds of this invention is determined by testing against a variety of pathogens using standard antibacterial dilution assays in Mueller-Hinton Agar, the activity being expressed as the Minimum Inhibitory Concentration (MIC, mcg./ml, 24 hours). The geometric mean MICs for many of the compounds of this invention are in the range of 0.125 to 2.0.

The serum levels of the compounds of the present invention can be determined by administering the compounds either intravenously, subcutaneously, or orally to the test animals. In general, serum levels are expressed as areas under the curve within a time period. The test compounds are generally administered intravenously at doses of 12.5 mg./kg., or subcutaneously at doses of 50 mg./kg., or orally at doses of either 100 mg./kg., or 400 mg./kg. The acute intraveneous toxicities of the compounds of this invention are determined in mice and are expressed as the dose which causes death of 50% of the animals.

The compounds of the present invention can be produced by a variety of multi-step syntheses, originating with tylosin, or any of the acylated derivatives known in the art.

Process A is illustrated schematically in Scheme A:

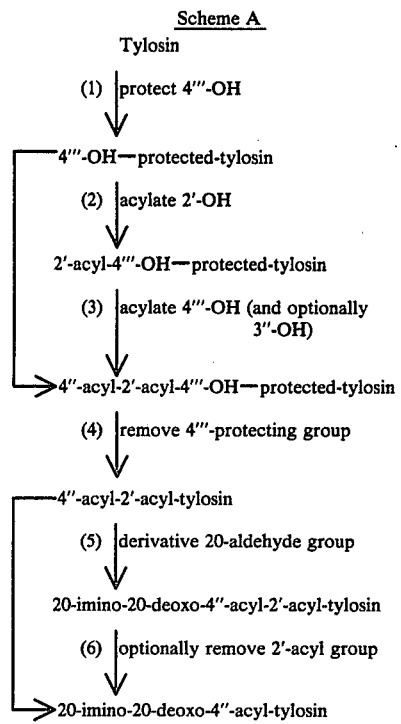

Process A begins by reacting tylosin with a suitable reagent to effect protection of the 4'''-hydroxyl group (Step A1). Although a variety of conventional hydroxyl-protecting groups can be utilized for this purpose (see for instance, U.S. Pat. No. 4,205,163), a highly preferred 4'''-hydroxyl protecting group for use in the present invention has been found to be the tert-butyldimethylsilyl group. As with other such protecting groups, it is most conveniently added to the 4'''-hydroxyl group by reacting the tylosin with tert-butyldimethylsilyl chloride in the presence of an acid acceptor such as imidazole, 4-dimethylaminopyridine, triethylamine or pyridine. Preferably, an anhydrous solvent such as dimethylformamide, dichloromethane or tetrahydrofuran is utilized as the reaction medium. The reaction occurs at temperatures of from about 10°–50° C., with room temperature being satisfactory in most cases.

Typical reaction times vary from about 12 to about 48 hours.

Step A2 of Process A involves the introduction of an acyl group at the 2'-hydroxyl position. It is necessary to block this hydroxy group prior to the introduction of any acyl group at the 3" or 4" position. Of course, where the acyl group to be introduced at the 4" position is identical to that of the 2'-acyl group, both may be simultaneously introduced, essentially combining Step A2 and Step A3 of Process A (as indicated in Scheme A as Step A2') simply by increasing the molar quantities of the acylating agent and adding a base such as pyridine as a catalyst. Selective acylation of the 2'-hydroxyl group may be carried out by the conventional methods known for such acylations of common macrolides. Acyl groups which may be employed for this purpose, are, for example, a lower alkanoyl group such as an acetyl, propionyl or butyryl group, a lower haloalkanoyl group such as a monochloroacetyl, trichloroacetyl, monobromoacetyl or trifluoroacetyl group, a lower alkoxycarbonyl group such as a methoxycarbonyl or ethoxycarbonyl group, and an aryloxyalkanoyl group such as a phenoxyacetyl group. As the acylating agent, carboxylic acids, acid halides and acid anhydrides corresponding to the acyl groups mentioned above are suitable for use in the process. Acetic anhydride is preferably utilized due to its yield and specificity of reaction. Most preferably, an anhydrous solvent, such as dry acetone is utilized as the reaction medium. Typical reaction temperatures vary from about 10°–50° C., with room temperature (about 25° C.) being preferred. Typical reaction times vary from about 10–48 hours, depending upon the nature of the specific reactants employed.

Step A3 of Process A concerns the introduction of the 4"-acyl group. The 4"-hydroxy group of the tylosin derivative acylated and protected at the 2' and 4"' positions is generally acylated easier than the 3-hydroxy group. When the 4"-hydroxy group is acylated according to the process of the present invention, a slight amount of 3,4"-diacyl derivative is sometimes formed as a by-product depending upon the acylating agent employed. The corresponding acid halides, acid anhydrides or mixed anhydrides with appropriate pivaloic acid are suitably used as the reactive derivatives of carboxylic acid compound in the process of this step. When an acid halide of a carboxylic acid or a mixed acid anhydride is employed as the acylating agent, the reaction of Step A3 is accomplished in the presence of a basic reagent. Preferred basic reagents are pyridine, 4-dimethylaminopyridine, picoline, piperidine and triethylamine, or mixtures thereof. A mixture of triethylamine and 4-dimethylaminopyridine is most highly preferred. Generally, the reaction is carried out in an inert organic solvent such as benzene, toluene, chloroform, dichloromethane, tetrahydrofuran or a mixture thereof. The basic reagent itself can be utilized as a solvent for the reaction. The temperature range is typically between −20° and 50° C., but a higher reaction temperature encourages by-product formation. Generally the preferred reaction temperature is between −10° C. and room temperature. Optionally, the 3"-hydroxyl group can also be acylated at this step. This 3"-hydroxyl group is a tertiary alcohol which reacts only under certain conditions. The 3-hydroxyl group must be blocked, preferably by use of the trimethylsilyl ether derivative, prior to the addition of the 3"-acyl group. Generally, conditions must be more severe than if only the 4"-position is acylated, i.e., at higher temperatures, i.e. 60°–100° C., and reaction times somewhat longer. Typically, an acyl chloride is utilized as the acylating agent and tribenzylamine as the basic agent. Any nonpolar, organic solvent is suitable for the conduct of the reaction. Of course, when the 3-position is blocked in a synthetic sequence, it must be deblocked at a later stage after the addition of the 3"-acyl group. Typically this is done after the completion of Step A3 or at any other convenient later stage in the synthetic sequence.

In Step A4 of Process A, the 4"'-hydroxyl protecting group is removed. The exact conditions for removal of course depend upon the nature of the protecting group introduced in Step A1. Such methods are well-known in the art. Where the highly preferred tert-butyldimethylsilyl group is utilized as the 4"'-hydroxyl protecting group, its removal is conveniently effected by utilizing tetra-n-butylammonium fluoride, or a similar source of fluoride ion. Typically, an anhydrous solvent such as tetrahydrofuran or diethyl ether is utilized as the reaction medium. A non-reactive gaseous atmosphere, such as argon, prevents by-products. Typical reaction temperatures range from 0° to 50° C., with typical reaction times ranging from 1–24 hours.

In Step A5 of Process A, the 20-aldehyde group of the compound is derivatized to the desired 20-imino-20-deoxo-4"-acyl-2'-acyl tylosin derivative. This is accomplished by reaction of the product of Step A4 with a 1-amino reactant of the formula

wherein $R_5$ is as hereinbefore defined. Many of the 1-amino reactants herein utilized are commercially available. Those that must be synthesized may be prepared by one of the procedures found in Biel. et.al., *J. Org. Chem.*, 26, 4096 (1961) or Gosl, et. al., *Org. Syn. Collect.*, Vol. V, 43 (1963). Generally, the reaction is conducted in a non-polar, anhydrous organic solvent such as benzene, toluene, chloroform, dichloromethane, tetrahydrofuran or a mixture thereof. Reaction temperatures range from about 0°–50° C., with room temperature being preferred. Reaction times vary from 12 hours to 10 days, depending upon the reactants employed.

Where the desired product lacks a 2'-acyl group, this group can be removed in the same step which derivatives the 20-aldehyde group by simply altering the reaction conditions of Step A5 slightly. Instead of a non-polar solvent, an alcoholic solvent such as methanol or ethanol, is utilized. The latter reaction times are shortened to about 1–3 days. Step A5' of Process A thus produces the desired 20-imino 20-deoxo-4"-acyl-tylosin.

The final and optional step (Step A6) of Process A involves the removal of the 2'-acyl group. The compounds of the present invention having a 2'-acyl group are metabolized in the mammalian body to the 2'-hydroxyl compound. Thus, removal of the 2'-acyl group is not absolutely necessary. However, when removal is desired, it is conveniently effected in a conventional manner, depending upon the exact nature of the 2'-acyl group. For instance, where acetyl is the 2'-acyl group, removal is typically effected by dissolving the compound in methanol and stirring at a temperature of 0°–50° C., (preferably room temperature) for a period of 1–5 days.

Steps A5 and A6 may also be performed in reverse order to effect removal of the 2'-acyl group prior to derivatization of the 20-aldehyde group.

Process B is illustrated schematically in Scheme B:

Scheme B
Tylosin (1) ↓ derivative 20-aldehyde group 20-imino-2-deoxo-tylosin (2) ↓ protect 4'''-OH (3') acylate 2',4''-OH 4'''-OH—protected-20-imino-20-deoxo-tylosin (3) ↓ acylate 2'-OH 2'-acyl-4'''-OH—protected-20-imino-20-deoxo-tylosin (4) ↓ acylate 4''-OH (and optionally 3''-OH)

4''-acyl-2'-acyl-4'''-OH—protected-20-imino-20-deoxo-tylosin (5) ↓ remove 4'''-protecting group 4''-acyl-2'-acyl-20-imino-20-deoxo-tylosin (6) ↓ optionally remove 2'-acyl group 4''-acyl-20-imino-20-deoxo-Tylosin Process B employs the same basic reaction steps as Process A, but their order of conduct is rearranged.

Step B1 of the process begins by reacting tylosin with a "1-amino reactant" of the formula $$H_2—R_5$$

wherein $R_5$ is as hereinbefore defined, to effect derivatization of the 20-aldehyde group to a 20-imino-20-deoxo group and thus produce a 20-imino-20-deoxo-tylosin. The reaction conditions employed in this Step B1 are essentially the same as those employed in Step A5 of Process A described above.

The 20-imino-20-deoxo-tylosin is then reacted in Step A2 with a suitable reagent to effect protection of the 4'''-hydroxyl group, thus producing a 4'''-hydroxyl-protected-20-imino-20-deoxo-tylosin. Step B2 employs typical reaction conditions such as those described for Step A1 of Process A. Of course, the 4'''-hydroxyl protecting group may be selected from any of the many well-known in the macrolide art, but, as described above, the tert-butyldimethylsilyl group is highly preferred for use in the present invention.

Having the 20-aldehyde protected as the 20-imino-20-deoxo derivative also has the advantage of eliminating aldehyde-derived by-products formed during the protection of the 4'''-hydroxyl group, thus affording significantly higher yields of the desired 4'''-hydroxyl-protected derivatives.

Step B3 of Process B acylates the 2'-hydroxyl group of the compound produced in the previous Step B2 so as to provide a 2'-acyl-4'''-hydroxyl-protected-20-imino-20-deoxo-tylosin. The reaction conditions for this acylation Step are essentially similar to those described above in Step A2 of Process A. Also, as indicated above, the acylations of Steps B3 and B4 may be combined in a single Step B3', simply by increasing the molar quantities of the acylating agent and adding a base such as pyridine as a catalyst, where the 2' and 4'' acyl groups are identical.

The 2'-acyl-4'''-hydroxyl protected-20-imino-20-deoxo-tylosin is then acylated at the 4''-hydroxyl position (and optionally the 3'' position) in Step B4 to produce a 4''-acyl-2'-acyl-4'''-protected-20-imino-20-deoxo-tylosin. Reaction conditions for the 4'- and 3''-acylations are substantially the same as those described above for Step A3 of Process A. As indicated in Process A, the 3-hydroxyl group must be blocked prior to addition of the 3'-acyl group.

Step B5 of Process B effects removal of the 4'''-hydroxyl protecting group to produce the desired 4''-acyl-2'-acyl-20-imino-20-deoxo-tylosin. This reaction is conducted under the same conditions as those utilized in Step A4 of Process A.

The final and optional step of Process B, Step B6, effects removal of the 2'-acyl group in a manner essentially the same as that described for Step A6 of Process A.

Process C is illustrated schematically in Scheme C:

Scheme C
Tylosin (1) ↓ derivative 20-aldehyde group 20-imino-20-deoxo-tylosin (2) ↓ acylate 3,2',4'' and 4'''-OH groups 3,2',4'',4'''-tetraacyl-20-imino-20-deoxo-tylosin (3) ↓ add new 4''-acyl group and transacylate old 4''-acyl to 3''-OH 4''-acyl-3,2',3'',4'''-tetraacyl-20-imino-20-deoxo-tylosin (4) ↓ remove 4''', 3 and 2'-acyl groups 4''-acyl-3''acyl-20-imino-20-deoxo-tylosin Process C begins, as does Process B, by converting tylosin into a 20-imino-20-deoxo-tylosin by reaction with a "1-amino-reactant" of the formula $$H_2—R_5$$

wherein $R_5$ is as hereinbefore defined. Reaction conditions for this Step C1 are essentially similar to those described above for Step B1 of Process B.

Step 2 of Process C involves acylation of the 3,2',4'' and 4'''-hydroxyl groups simultaneously. This is accomplished using reaction times and temperatures similar to those described above for Steps A2 and A3 of Process A and Steps B3 and B4 of Process B, but the molar amounts of acylating agent and basic agent are greatly increased, usually to about 5–20 equivalents. This step thus produces a 3,2',4'',4'''-tetraacyl-20-imino-2-deoxo-tylosin.

Step 3 of Process C effects replacement of the 4''-acyl group with another 4''-acyl group and transacylates the original 4''-acyl group to the 3''-hydroxyl. This transacylation is made possible by the differences in reactivity between the secondary 4''-hydroxyl group and the tertiary 3″-cis-hydroxyl group. [See, for instance, Jaret et al., *J. Chem. Soc.*, (C), 1374 (1973)]. A large molar excess (typically 5–10 equivalents) of the new acylating agent is utilized as well as temperatures ranging from 80° C. to reflux temperature of the solvent. Typically, pyridine is utilized as the solvent and also performs the role of basic agent so that the reaction is conducted at about 110° C. (reflux of pyridine). Typical reaction times vary from about 12 to 24 hours. This Step C3 thus provides a 4″-acyl-3,2′,3‴,4‴tetracyl-20-imino-20-deoxo-tylosin where the 4″-acyl group differs from the 3,2′,3‴,4‴-acyl groups.

In Step C4, removal of the 4‴, 3 and 2′ acyl groups is effected by the addition of an organic base, typically triethylamine. Typical solvents are those such as methanol and typical temperatures are in the range of 25°–60° C. The reaction is monitored to determine completion of the removal of the 4‴, 3 and 2′-acyl groups and production of the desired 4″-acyl-4″-acyl -20-imino-20-deoxo-tylosin. Process D is illustrated schematically in Scheme D:

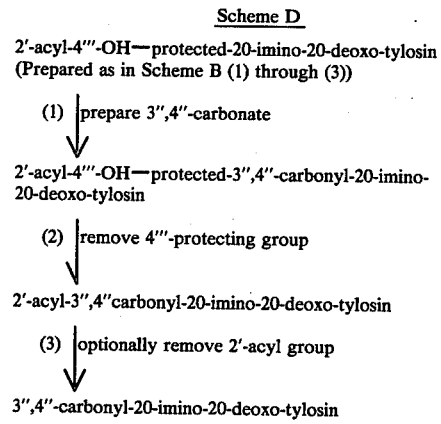

Scheme D

2′-acyl-4‴-OH—protected-20-imino-20-deoxo-tylosin
(Prepared as in Scheme B (1) through (3))

(1) prepare 3″,4″-carbonate

2′-acyl-4‴-OH—protected-3″,4″-carbonyl-20-imino-20-deoxo-tylosin (2) remove 4‴-protecting group 2′-acyl-3″,4″carbonyl-20-imino-20-deoxo-tylosin (3) optionally remove 2′-acyl group 3″,4″-carbonyl-20-imino-20-deoxo-tylosin Process D begins, as does Process B, by converting tylosin into a 2′-acyl-4-‴-hydroxyl protected-20-imino-20-deoxo-derivative using the methods described above for Steps B1 through B3 of Process B. The 2′-acyl-4‴-hydroxyl protected-20-imino-20-deoxy-tylosin is then converted into a 2′-acyl-4‴-hydroxyl protected-3″,4″-carbonyl-20-imino-20-deoxo-tylosin in Step D1. The reagent used to effect Step D1 is N,N′-carbonyldiimidazole in an inert solvent such as anhydrous dichloromethane. Typically, the reaction is conducted at 0°–30° C., for times ranging from 12–30 hours.

Step D2 of Process D effects removal of the 4‴-hydroxyl group to produce the desired 2′-acyl-3″, 4″-carbonyl-20-imino-20-deoxo-tylosin. This reaction is conducted under the same conditions as those utilized in Step A4 of Process A.

The final and optional step of Process D, Step D3, effects removal of the 2′-acyl group in a manner essentially the same as that described in Step A6 of Process A.

The following examples describe in detail compounds illustrative of the present invention. It will be apparent to those skilled in the art that many modifications, both of materials and methods, may be practiced without departing from the purpose and intent of this invention. In these examples, "Rotation" denotes optical rotation; "UV" denotes ultraviolet spectra; "IR" denotes infrared spectra; and "NMR" denotes nuclear magnetic resonance spectra.

EXAMPLE 1

A. 4‴-O-(tert-Butyldimethylsilyl)-tylosin

Tylosin (25 g) and imidazole (18.6 g) are dissolved in dry dimethylformamide (250 ml) and tert-butyldimethylsilyl chloride (19.7 g) is added. The solution is allowed to remain at 25° C. for 19 hours. Then the solution is evaporated to dryness and the residue is taken up in chloroform, washed with water, dried (MgSO$_4$) and filtered. The filtrate is evaporated to dryness and the residue triturated with hot hexane (3×1). The insoluble residue is then chromatographed on a silica gel column (160×5 m) using 1.5% methanol in chloroform as the eluant to give 4‴-O-(tert-butyldimethylsilyl)-tylosin, as a colorless, amorphous solid, having characteristics as follows:

Rotation: $[\alpha]_D^{26} -41.8°$ (CHCl$_3$); UV: $\lambda_{max}$ (CF$_3$CH$_2$OH) 284 nm ($\epsilon$22,616), IR: $\nu_{max}$ (CHCl$_3$) 3500, 2980, 2950, 2910, 1722, 1682, 1600, 1320, 1662, 1220, 1050 cm$^{-1}$; NMR: $\delta_H$ (CDCl$_3$) 0.14 (3H,s, 4‴-SiCH$_3$), 0.17 (3H,s,4‴-SiCH$_3$), 0.97 (9H,s,4‴-SiC(CH$_3$)$_3$), 1.80 (3H, d, J$_{13,22}$ 1.5 Hz, 22-CH$_3$), 2.50(6H, s, 3′-N (CH$_3$)$_2$) 3.51 (3H,s,2‴-OCH$_3$), 3.62(3H,s,3‴-OCH$_3$), 4.23(1H,d,J$_{1, 2'}$ 7.5 Hz, H$_{1'}$), 4.62(1H,d,J$_{1''',2'''}$7.5 Hz H$_{1'''}$), 5.95(1H,dq,J$_{13,22}$ 1.5 Hz, J$_{1314}$ 10 Hz, H$_{13}$), 6.25(1H, d, J$_{10,11}$ 15 Hz, H$_{10}$), 7.34(1H,d,J$_{10,11}$ 15 Hz, H$_{11}$) and 9.77 (1H,s, H$_{20}$).

B. 2′-O-Acetyl-4‴-O-(tert-butyldimethylsilyl)-tylosin

4‴-O-(tert-Butyldimethylsilyl)-tylosin (15g) is dissolved in dry acetone (500 ml) and acetic anhydride (7.4g) is added. The mixture is allowed to remain at 25° C. for 17 hours. The solution is then evaporated to dryness and the residue azeotroped with toluene to give 2′-O-acetyl-4‴-O-(tert-butyldimethylsilyl)-tylosin as a colorless, amorphous solid. An analytical sample is purified by chromatography on a silica gel column (70×2.5 cm) using 20% acetone in hexane as the eluant. The product has characteristics as follows:

Rotation: $[\alpha]_D^{26} -45.4°$ (CH$_3$OH); UV: $\pi_{max}$ (CF$_3$CH$_2$OH) 285 nm ($\epsilon$22,784); IR: $\nu_{max}$ (CDCl$_3$) 3530, 2980, 2960, 2920, 1743, 1720, 1680, 1590, 1230, 1160, 1045 cm$^{-1}$; NMR: $\delta_H$ (CDCl$_3$) 0.10(3H,s,4‴-SiCH$_3$), 0.13 (3H,s,4‴-SiCH$_3$), 0.94(9H,s,4‴-Si C(CH$_3$)$_3$), 1.78(3H,d, J$_{13,22}$ 1.5 Hz, 22-CH$_3$), 2.06(3H,s,2′-OCOCH$_3$), 2.38(6H,s,3′-N(CH$_3$)$_2$), 3.48(3H,s,2‴OCH$_3$), 3.59(3H,s,3‴-OCH$_3$), 4.27(1H,d,J$_{1',2'}$ 7.5 Hz,H$_{1'}$), 4.60(1H,d,J$_{1''',2'''}$ 8 Hz,H$_{1'''}$), 5.92 (1H,dq,J$_{13,14}$10.5 Hz, J$_{13,22}$1.5 Hz,H$_{13}$), 6.25 (1H,d, J$_{10,11}$ 15 Hz,H$_{10}$), 7.31(1H,d,J$_{10,11}$ 15 Hz, H$_{11}$) and 9.65(1H,s,H$_{20}$).

C. 2′-O-Acetyl-4‴-O-(tert-butyldimethylsilyl)-4′-O-isovaleryltylosin

2′-O-Acetyl-4‴-O-(tert-butyldimethylsilyl)-tylosin (prepared as in part B of this example) (15.6 g), 4-dimethylaminopyridine (1.85 g) and triethylamine (30 ml) are dissolved in dry dichloromethane (1 l.). iso-Valeric anhydride (2.82 g), in dry dichloromethane (200 ml), is added dropwise, with stirring, at 25° C. over one hour. The solution is then stirred for a further 16 hours at 25° C. The solution is washed with water, dried (MgSO$_4$), filtered and evaporated to dryness. The residue is then chromatographed on a silica gel column (160×5 cm)

using 30% ethyl acetate in dichloromethane as the eluant to give in order of elution, 2'-O-acetyl-4'''-O-(tert-butyldimethylsilyl)-4''-O-iso-valeryltylosin as a colourless, amorphous solid, having characteristics as follows:

Rotation: $[\alpha]_D^{26} -51.7°$ (CHCl$_3$); UV: $\lambda_{max}$ (CF$_3$CH$_2$OH) 285 nm ($\epsilon$23,323); IR:$\nu_{max}$ (CDCl$_3$) 3520, 2980, 2950, 2900, 1740, 1720, 1675, 1590, 1235, 1160, 1050 cm$^{-1}$, NMR: $\delta_H$ (CDCl$_3$) 0.10(3H,s,4'''-SiCH$_3$), 0.13(3H,s,4'''SiCH$_3$), 0.94(9H,s,4'''-SiC(CH$_3$)$_3$), 0.98(6H,d,J6 Hz, 4''-OCOCH$_2$CH(CH$_3$)$_2$), 1.78(3H,d,J$_{13,22}$ 1.5Hz,22-CH$_3$), 2.06(3H,s,2'-OCOCH$_3$), 2.40(6H,s,3'-N(CH$_3$)$_2$), 3.48(3H, s,2'''-OCH$_3$), 3.58(3H,s,3'''-OCH$_3$), 4.25(1H,d,J$_{1',2'}$ 7.5 Hz,H$_{1'}$), 4.59(1H,d,J$_{1''',2'''}$ 8 Hz,H$_{1'''}$), 5.91(1H,dd, J$_{13,22}$ 1.5 Hz,J$_{13,14}$ 10.5 Hz,H$_{13}$), 6.24(1H,d, J$_{10,11}$ 15.5 Hz,H$_{10}$), 7.31(1H,d,J$_{10,11}$ 15.5 Hz, H$_{11}$) and 9.65(1H,s,H$_{20}$), and unreacted 2'-O-acetyl-4'''-O-(tert-butyldimethylsilyl)tylosin.

D. 2'-O-Acetyl-4''-O-iso-valeryltylosin

2'-O-Acetyl-4'''-O-(tert-butyldimethylsilyl)-4''-O-iso-valeryltylosin (prepared as in part C of this example) (8.25 g) and anhydrous tetra-n-butylammonium fluoride (obtained by azeotroping the trihydrate (2.2 g) with toluene), are dissolved in dry tetrahydrofuran (400 ml) and the solution is allowed to remain at 25° C. for 16 hours under dry argon gas. The solution is evaporated to dryness and the residue taken up in dichloromethane, washed with water, dried (MgSO$_4$), filtered and evaporated to dryness. The residue is chromatographed on a silica gel column (160×2.5 cm) using 40% acetone in hexane as the eluant to give the product, 2'-O-acetyl-4''-O-iso-valeryltylosin as a colourless amorphous solid, having the following characteristics:

Rotation: $[\alpha]_D^{26} -66.6°$ (CHCl$_3$); UV: $\lambda_{max}$(CH$_3$OH) 282 nm ($\epsilon$22,641); IR: $\nu_{max}$ (CDCl$_3$) 3550, 2980, 2950, 2900, 1740, 1735, 1730, 1680, 1600, 1248, 1175, 1065 cm$^{-1}$; NMR: $\delta$H (CDCl$_3$), 0.98(6H,d, J 6 Hz, 4''-OCOCH$_2$CH(CH$_3$)$_2$), 1.78(3H,d,J$_{13,22}$ 1.5 Hz,22-CH$_3$), 2.07(3H,s,2'-OCOCH$_3$), 2.41(6H,s, 3'-N(CH$_3$)$_2$), 3.50(3H,s,2'''-OCH$_3$), 3.63(3H,s, 3'''-OCH$_3$), 5.95(1H,dq,J$_{13,22}$ 1.5 Hz,J$_{13,14}$ 10.5 Hz, H$_{13}$), 6.31(1H,d,J$_{10,11}$ 15.5 Hz,H$_{10}$), 7.36(1H,d, J$_{10,11}$ 15.5Hz,H$_{11}$) and 9.70(1H,s,H$_{20}$).

E. 2'-O-Acetyl-20-deoxo-20-[(4,4-dioxothiomorpholinyl)-imino]-4''-O-iso-valeryltylosin 2'-O-Acetyl-4''-O-iso-valeryltylosin (prepared as in part D of this example) (1.8 g) and 1-N-amino-4,4-dioxothiomorpholine (458 mg) are dissolved in dry dichloromethane (50 ml) and the mixture stirred at 25° C. for 212 hours. The solution is evaporated to dryness and the residue chromatographed on a silica gel column (110×2.5 cm) at maximum flow rate using 30% acetone in hexane as the eluant to give 2'-O-acetyl-20-deoxo-20-[(4,4-dioxothiomorpholinyl)-imino]-4''-O-iso-valeryl-tylosin as a colourless amorphous solid, having the following characteristics:

Rotation: $[\alpha]_D^{26} -71.3°$ (CHCl$_3$); UV: $\lambda_{max}$(CH$_3$OH) 240 nm ($\epsilon$8,033), 283 nm ($\epsilon$23,102); IR: $\nu_{max}$ (CDCl$_3$) 3510, 2980, 2950, 2900, 1740, 1720, 1680, 1600, 1223, 1192, 1172, 1130, 1060 cm$^{-1}$; NMR: $\delta_H$ (CDCl$_3$), 0.98(6H, d,J 6 Hz,4''-OCOCH$_2$CH(CH$_3$)$_2$), 1.78(3H,d, J$_{13,22}$ 1.5 Hz, 22-CH$_3$), 2.06(3H,s,2'-OCOCH$_3$), 2.40(6H,s,3'-N(CH$_3$)$_2$), 3.48(3H,s,2'''-OCH$_3$), 3.62(3H,s,3'''-OCH$_3$), 5.90(1H, dq,J$_{13,22}$ 1.5 Hz, J$_{13,14}$ 10 Hz,H$_{13}$), 6.25(1H,d, J$_{10,11}$ 15 Hz,H$_{10}$), 7.97(1H,m,H$_{20}$) and 7.34(1H,d, J$_{10,11}$ 15 Hz, H$_{11}$).

F. 4''-O-iso-Valeryltylosin

2'-O-Acetyl-4''-O-iso-valeryltylosin (854 mg.) is dissolved in methanol (100 ml) and the solution is allowed to remain at 25° C. for 91 hours. The solution is evaporated to dryness and the residue chromtographed on a silica gel column (110×2.5 cm.) using 35% acetone in hexane as the eluant to give 4''-O-iso-valeryltylosin, as a colourless amorphous solid, having the following:

Rotation $[\alpha]_D^{26} -56.0°$ (CHCl$_3$), $\lambda_{max}$ (CH$_3$OH) 282 mm ($\epsilon$21,723); IR: $\nu_{max}$ (CDCl$_3$); 3500, 2970, 2930, 2880, 1725, 1680, 1595, 1165, 1050 cm.$^{-1}$, $\delta_H$ (CDCl$_3$) 0.98(6H,d,J6 Hz, 4''-OCOCH$_2$CH(CH$_3$)$_2$), 1.79 (3H,d,J$_{13,22}$ 1.5 Hz, 22-CH$_3$), 2.52(6H,s,3'-N(CH$_3$)$_2$), 3.50(3H,s,2'''-OCH$_3$), 3.62(3H,s,3'''-OCH$_3$), 4.21(1H,d,J$_{1',2'}$8 Hz,H$_{1'}$), 4.54(1H,d, J$_{1''',2'''}$0 7.5 Hz, H$_{1'''}$), 5.88(1H,dq, J$_{13,22}$ 1.5 Hz, J$_{13,14}$ 10.5 Hz, H$_{13}$), 6.23 (1H,d,J$_{10,11}$ 15.5 Hz, H$_{10}$), 7.31(1H,d,J$_{10,11}$) and 9.68(1H,s,H$_{20}$).

EXAMPLE 2

A. 20-Deoxo-20-[(4,4-dioxothiomorpholinyl)-imino]tylosin

Tylosin (30 g) and 1-N-amino-4,4-dioxothiomorpholine (4.92 g) are dissolved in absolute ethanol (310 ml) and the mixture is stirred at 25° C. for 42 hours. The solution is evaporated to dryness. The residue is then chromatographed on a silica gel column (120×5 cm) using 2% methanol in chloroform as the eluant, followed by rechromatography of the overlap fractions on a silica gel column (120×5 cm) using 1.5% methanol in chlorform as the eluant, to give 20-deoxy-20-[(4,4-dioxothiomorpholinyl)-imino]-tylosin as a colourless amorphous solid, having the following characteristics:

Rotation: $[\alpha]_D^{26} -56.8°$ (CHCl$_3$); UV: $\lambda_{max}$ (CF$_3$CH$_2$OH) 235 nm ($\epsilon$6,626), 286 nm ($\epsilon$21,765); IR: $\nu_{max}$ (CDCl$_3$) 3580, 2980, 2950, 2900, 1710, 1675, 1585, 1305, 1160, 1120, 1040 cm$^{-1}$; NMR: $\delta_H$ (CDCl$_3$) 0.94(3H,t,J$_{16,17}$ 7 Hz, 17-CH$_3$), 1.02(3H,d,J$_{4,18}$ 6 Hz,18-CH$_3$), 1.80(3H, d,J$_{13,22}$ 1.5 Hz,22-CH$_3$), 2.50(6H,s,3'-N(CH$_3$)$_2$), 3.50(3H,s,2'''-OCH$_3$), 3.63(3H,s,3'''OCH$_3$), 4.29(1H, d,J$_{1',2'}$ 7 Hz,H$_{1'}$), 4.58(1H,d,J$_{1''',2'''}$ 7.5 Hz,H$_{1'''}$), 5.94(1H,dq, J$_{13,22}$ 1.5 Hz,J$_{13,14}$ 10 Hz,H$_{13}$), 6.30 (1H,d, J$_{10,11}$ 15.5 Hz, H$_{10}$), 7.01(1H,t,J$_{19,20}$ 5 Hz,H$_{20}$) and 7.37(1H,d,J$_{10,11}$ 15.5 Hz,H$_{11}$).

B. 4'''-O-(tert-Butyldimethylsilyl)-20-deoxo-20-[(4,4-dioxothiomorpholinyl)-imino]-tylosin 20-Deoxo-20-[(4,4-dioxothiomorpholinyl)-imino]-tylosin (prepared as in part A of this example) (3 g.) and imidazole (975 mg.) are dissolved in dry dimethylformamide (45 ml.) and tert-butyldimethylsilyl chloride (2.16 g.) is added. The mixture is stirred at 25° C. for 18 hours under dry argon gas. The solution is evaporated to dryness and the residue is taken up in dichloromethane, washed with water, dried (MgSO$_4$), filtered and evaporated. The residue is then chromatographed on a silica gel column (30×5 cm.) using 30% acetone in hexane as the eluant to give 4'''-O-(tert-butyldimethylsilyl)-20-deoxo-20-[(4,4-dioxothiomorpholinyl)-imino]-tylosin as a colorless, amorphous solid, having:

Rotation: $[\alpha]_D^{26} -47.1°$ (CHCl$_3$); UV: $\lambda_{max}$ (CF$_3$CH$_2$OH) 235 nm ($\epsilon$6,710), 286 nm ($\epsilon$23,082); IR: $\nu_{max}$ (CDCl$_3$) 3500, 2970, 2940, 2900, 1740, 1680, 1595, 1315, 1260, 1130, 1052 cm.−1; NMR: $\delta_H$ (CDCl$_3$) 0.09 (3H,s,4'''-SiCH$_3$), 0.12(3H,s,4'''-SiCH$_3$), 0.94 (9H,s,4'''-SiC(CH$_3$), 1.79 (3H,d,J$_{13,22}$ 1.5 Hz, 22-CH$_3$), 2.50(6H,s,3'N(CH$_3$)$_2$), 3.50 (3H,s,2'''-OCH$_3$),3.61 (3H,s,3'''OCH$_3$), 4.28 (1H,d, J$_{1',2'}$ 8 Hz, H$_{1'}$), 5.95 (1H,dq, J$_{13,22}$ 1.5 Hz, J$_{13,14}$ 10 Hz, H$_{13}$), 6.28 (1H,d, J$_{10,11}$ 15.5 Hz, H$_{10}$), 7.00 (1H,t,J$_{19,20}$ 5 Hz,H$_{20}$) and 7.36 (1H,d,J$_{10,11}$ 15.5 Hz,H$_{11}$).

C.

2'-O-Acetyl-4'''-O-(tert-butyldimethylsilyl)-20-deoxo-20-[(4,4-dioxothiomorpholinyl)-imino]-tylosin 4'''-O-(tert-Butyldimethylsilyl)-20-deoxo-20-[(4,4-dioxothiomorpholinyl)-imino]-tylosin (prepared as in part C of this example) (1.41 g.) is dissolved in dry acetone (30 ml.) and acetic anhydride (0.5 ml.) is added. The mixture is allowed to remain at 25° C. for 40 hours. The solution is evaporated to dryness and the residue azeotroped with toluene. The residue is taken up in a mixture of dichloromethane-water and the pH adjusted to 9.5 with dilute aqueous sodium hydroxide. The dichloromethane layer is washed with water, dried (MgSO$_4$), filtered and evaporated to dryness to give 2'-O-acetyl-4'''-O-(tert-butyldimethylsilyl)-20-deoxo-20-[(4,4-dioxothiomorpholinyl)-imino]-tylosin, as a colorless, amorphous solid. An analytical sample (200 mg.), prepared by chromatography on a silica gel column (60×2 cm.) using 30% acetone in hexane as the eluant, having Rotation: [α]$_D^{26}$ −52.2° (CHCl$_3$); UV: λ$_{max}$ (CF$_3$CH$_2$OH) 234 nm (ε6,369), 286 nm (ε22,441); IR: ν$_{max}$ (CDCl$_3$) 3500, 2975, 2950, 2900, 1750, 1715, 1680, 1598, 1318, 1240, 1130, 1055, cm.−1; NMR: $\delta_H$(CDCl$_3$) 0.09 (3H,s,4'''-SiC(CH$_3$)$_3$), 0.12(3H,s,4'''-SiCH$_3$), 0.92(9H,s,4'''-SiC(CH$_3$)$_3$), 1.77(3H,d,J$_{13,22}$ 1.5 Hz,22-CH$_3$), 2.07 (3H,s,2'-OCOCH$_3$), 2.40 (6H,s,3'-N(CH$_3$)$_2$), 3.49(3H,s,2'''-OCH$_3$), 3.61 (3H,s,3'''-OCH$_3$), 4.34 (1H,d,J$_{1',2'}$ 8Hz, H$_{1'}$), 4.62 (1H,d,J$_{1''',2'''}$8Hz, H$_{1'''}$), 5.96 (1H,dq, J$_{13,22}$ 1.5 Hz,J$_{13,14}$ 10.5 Hz, H$_{13}$), 6.31 (1H, d,J$_{10,11}$ 15 Hz,H$_{10}$), 6.99(1H,t,J$_{19,20}$ 5 Hz, H$_{20}$) and 7.38 (1H,d,J$_{10,11}$ 15 Hz, H$_{11}$).

D.

2'-O-Acetyl-4'''-O-(tert-butyldimethylsilyl)-20-deoxo-20-[(4,4-dioxothiomorpholinyl)-imino]-4''-O-iso-valeryltylosin 2'-O-Acetyl-4'''-O-(tert-butyldimethylsilyl)-20-deoxy-20-[(4,4-dioxothiomorpholinyl)-imino]-tylosin (6 g.),4-dimethylaminopyridine (609 mg.) and triethylamine (3 ml.) are dissolved in dry dichloromethane (50 ml.). iso-Valeric anhydride (927 mg.) in dry dichloromethane (200 ml.) is added dropwise to the stirred solution at 25° C. over a period of 1.5 hours. The mixture is stirred at 25° C. for an additional 18 hours. Water is added to the solution and the pH adjusted to 9.5 with dilute aqueous sodium hydroxide. The dichloromethane layer is washed with water, dried (MgSO$_4$), filtered and evaporated to dryness. The residue is then chromatographed on a Waters Prep 500 HPLC instrument using one silica gel cartridge and 22% acetone in hexane as the eluant, to give 2'-O-acetyl-4'''-O-(tert-butyldimethylsilyl)-20-deoxy-20-[(4,4-dioxothiomorpholinyl)-imino]-4''-O-iso-valeryltylosin as a colourless, amonphous solid, having Rotation: [α]$_D^{26}$ −53.4° (CHCl$_3$); UV: λ$_{max}$ (CF$_3$CH$_2$OH) 234 nm (6,462), 286 nm (ε22,950); IR: ν$_{max}$ (CDCl$_3$) 3510, 2975, 2940, 2900, 1740, 1720, 1680, 1599, 1315, 1240, 1190, 1170, 1125, 1060 cm.−1; NMR: $\delta_H$ (CDCl$_3$) 0.11 (3H,s,4'''-SiCH$_3$), 0.13 (3H,s,4'''-SiCH$_3$), 0.92 (9H,s,4'''-SiC(CH$_3$)$_3$,) 0.97 (6H,d,JHz, 4''OCOCH$_2$CH(CH$_3$)$_2$), 1.79 (3H,d,J$_{13,22}$ 1.5 Hz, 22-CH$_3$), 2.09 (3H,s,2'-OCOCH$_3$), 2.43 (6H,s, 3'-N(CH$_3$)$_2$), 3.51 (3H,s,2'''-OCH$_3$), 3.63 (3H,s,3'''-OCH$_3$), 5.97 (1H,dq,J$_{13,22}$ 1.5 Hz, J$_{13,14}$ 10 Hz, H$_{13}$), 6.33 (1H,d,J$_{10,11}$ 15 Hz,H$_{10}$), 6.98 (1H,t,J$_{19,20}$ 5 HzH$_{20}$) and 7.39 (1H,d,J$_{10,11}$ 15 Hz,H$_{11}$). The more polar fractions are found to be unreacted 2'-O-acetyl-4'''-O-(tert-butyldimethylsilyl)-20-deoxy-20-[(4,4-dioxothiomorpholinyl)-imino]-tylosin.

E.

2'-O-Acetyl-20-deoxo-20-[(4,4-dioxothiomorpholinyl)-imino]-4''-O-iso-valeryltylosin 2'-O-Acetyl-4'''-O-(tert-butyldimethylsilyl)-20-deoxo-20-[(4,4-dioxothiomorpholinyl)-imino]-4''-O-iso-valeryltylosin (prepared as in part D of this example) (500 mg.) and anhydrous tetra-n-butylammonium fluoride obtained by azeotroping the trihydrate (122 mg.) with toluene, are dissolved in dry tetrahydrofuran (100 ml.) and the solution is allowed to remain at 25° C. for 16 hours. The solution is evaporated to dryness and the residue is taken up in dichloromethane, washed with water, dried (MgSO$_4$), filtered and evaporated to dryness. The residue is then chromatographed on a silica gel column (110×2.5 cm.) using 30% acetone in hexane as the eluant to give 2'-O-acetyl-20-deoxo-20-[(4,4-dioxothiomorpholinyl)-imino]-4''-O-iso-valeryltylosin as a colourless, amorphous solid, identical with that prepared in Example 1.

EXAMPLE 3

20-Deoxo-20-[(4,4-dioxothiomorpholinyl)imino]-4''-O-iso-valeryltylosin

2'-O-Acetyl-20-deoxo-20-[(4,4-dioxothiomorpholinyl)-imino]-4''-O-iso-valeryltylosin (prepared as in parts A through E of Example 1 or Example 2) (200 mg.) is dissolved in methanol (30 ml.) and the solution stirred at 25° C. for 91 hours. The solution is evaporated to dryness and the residue is chromatographed or a silica gel column (40×2.5 cm.) at maximum flow rate using 30% acetone in hexane as the eluant to give 20-deoxo-20-[(4,4-dioxothiomorph-olinyl)-imino]-4"-O-iso-valeryltylosin as a colourless amorphous solid, having: Rotation: [α]$_D^{26}$ −62.1° (CHCl$_3$); UV: λ$_{max}$ (CH$_3$OH) 240 nm (ε7,577), 283 nm (ε23,153); IR: ν$_{max}$ (CDCl$_3$) 3510,2975, 2950, 2900, 1725, 1685, 1600, 1320, 1190, 1170, 1130, 1060 cm.$^1$, NMR: δ$_H$ (CDCl$_3$) 0.98 (6H,d,J 6 Hz, 4"-OCOCH$_2$CH(CH$_3$)$_2$), 1.80 (3H,d, J$_{13,22}$ 1.5 Hz, 22-CH$_3$), 2.53 (6H,s,3'-N(CH$_3$)$_2$), 3.50 (3H,s,2'''-OCH$_3$), 3.64 (3H,s,3'''-OCH$_3$), 4.30 (1H,d, J$_{1',2'}$ 7 Hz, H$_{1'}$), 4.58 (1H,d,J$_{1''',2'''}$ 7 Hz,H$_{1'''}$), 5.94 (1H,dq,J$_{13,22}$ 1.5 Hz, J$_{13,14}$ 10 Hz, H$_{13}$), 6.30 (1H,d,J$_{10,11}$ 15 Hz, H$_{10}$), 7.00 (1H,5,J$_{19,20}$ 5 Hz,H$_{20}$) and 7.38 (1H,d,J$_{10,11}$ 15 Hz, H$_{11}$).

EXAMPLE 4

20-Deoxo-20-[(4,4-dioxothiomorpholinyl)-imino]-4"-O-iso-valeryltylosin

2'-O-Acetyl-4"-O-iso-valeryltylosin (prepared as in steps A through D of Example 1) (700 mg.) and 1-N-amino-4,4-dioxothiomorpholine (101 mg.) are dissolved in dry methanol (100 ml.) and the mixture is stirred at 25° C. for 75 hours. The solution is evaporated to dryness and the residue chromatographed on a silica gel column (110×2.5 cm.) at maximum flow rate using 30% acetone in hexane as the eluant. Thus produced is 20-deoxo-20-[(4,4-dioxothiomorpholinyl)-imino]-4"-O-iso-valeryltyosin, identical to that prepared in Example 2.

Example 5

A.
2',4"-Di-O-acetyl-4'''-O-(tert-butyldimethylsilyl)-tylosin

4'''-O-(tert-Butyldimethylsilyl)tylosin (prepared as in part A of Example 1) (1 g.) is dissolved in dry pyridine (50 ml.) and acetic anhydride (392 mg.) is added. The mixture is then allowed to remain at 25° C. for 17 hours. The solution is evaporaed to dryness and the residue azetroped with toleuene. The residue is then dissolved in dichloromethane, washed with water, dried (MgSO$_4$), filtered and evaporated to dryness. Chromotagraphy of the residue on a silica gel column (110×2.5 cm.) using 30% acetone in hexane as the eluant, gives 2', 4"-di-O-acetyl-4'''-O-(tert-butyldimenhysilyl)-tylosin, as a colourless amorphous solid, having the following characteristics:
Rotation: [α]D$^{26}$−52.1° (CHCl$_3$); UV:λ$_{max}$(CH$_3$OH) 283nm (ε22,449), IR:ν$_{max}$ (CDCl$_3$) 3520, 2980, 2950, 2900, 1740, 1720, 1680, 1590, 1235,1160, 1045 cm$^{31}$ $^1$; NMR: δ $_H$ (CDCl$_3$), 0.12(3H,s,4'''-SiCH$_3$), 0.14(3H,s, 4'''SiCH$_3$), 0.96(9H,s,4'''-SiC(CH$_3$)3), 1.80(3H,d, J$_{13,22}$ 1.5Hz,22-CH$_3$), 2.06(3H,s,2'-OCOCH$_3$), 2.15(3H,s,4"-OCOCH$_3$), 2.42(6H,s,3'-N(CH$_3$), 3.50 (3H,s,2'''-OCH$_3$), 3.60(3H,s,3'''-OCH$_3$), 5,93(1H,dq,J$_{13}$, 22 1.5Hz,J$_{13,14}$10.5Hz,H$_{13}$), 6.26(1H,d,J$_{10,11}$ 15.5Hz, H$_{10}$), 7.32(1H,d,J$_{10,11}$15.5Hz, H$_{11}$) and 9.67(1H,s,H$_{20}$),

B. 2',4"-Di-O-acetyltylosin

2',40"-Di-O-acetyl-4'''-O-(tert-butyldimethylsilyl)-tylosin (prepared as in part A of this Example) (1.87 g.) and anhydrous tertra-n-butylammonium fluoride (obtained by azeotroping the trihydrate (497 mg.) with toluene, are dissolved in dry tetrahydrofuran (100 ml.) and the solution is allowed to remain at 25° C. for 16 hours under dry argon gas. The solution is evaporated to dryness and he residue taken up in dichloromethane, washed with water, dried (MgSO$_4$), filtered and evapoated to dryness to afford the product, 2', 4"-di-O-acetyltylosin.

C. 4-O-Acetyltylosin

The crude 2',40"-di-O-acetyltylosin (prepared as in part B of this Example) is dissolved in methanol (100 ml.) and the solution allowed to remain at 25° C. for 25 hours. The solution is evaporated to dryness and the residue chromatographed on a silica gel column (160×2.5 cm.) using 20% increasing to 35% acetone in hexane as the eluant, to afford in order of elution unreacted 2',4"-di-O-acetyltylosin as a colourless,amorphous solid, havin Rotation: [α]D$^{26}$−67.7° (CHCl$_3$); UV:λ$_{max}$ (CH$_3$OH) 282 nm (ε22,270); IR:ν$_{max}$ (CDCl$_3$) 3500, 2980, 2940, 2880, 1730, 1690, 1595, 1240, 1220, 1167, 1060, cm.−$^1$; NMR: δ $_H$(CDCl$_3$) 1.78 (3H,d,J$_{13,22}$−1,5 Hz,22-CH$_3$), 2.06 (3H,s,2'-OCOCH$_3$), 2.13 (3H,s,4"-OCOCH$_3$), 2.40 (6H,s, 3'-N(CH$_3$)$_2$), 3.46 (3H,s,2'''-OCH$_3$), 3.62 (3H,s,3'''-OCH$_3$), 5.89 (1H,dq,J$_{13,22}$1.5Hz, J$_{13,14}$ 10.5Hz,H$_{13}$), 6.24 (1H,d,J$_{10,11}$15.5Hz, H$_{10}$), 7.31 (1H,d,J$_{10,11}$ 15.5Hz, H$_{11}$) and 9.64 (1H,s,H$_{20}$), and 4"-O-acetyltylosin as a colourless,amorphous solid, having:
Rotation: [α]D$^{26}$−57.4° (CHCl$_3$); UV:λ$_{max}$(CH$_3$OH) 282 nm (22,136); IR:$_{max}$(CDCl$_3$) 3500, 2980, 2940, 2900, 1720, 1680, 1593, 1245, 1168, 1055 cm.−$^1$; NMR: $_H$ (CDCl$_3$) 1.78 (3H,d,J$_{13,22}$1.5 Hz, 22-CH$_3$), 2.13 (3H,s,4"-OCOCH$_3$), 2.52 (6H,s,3'-N(CH$_3$)$_2$), 3,47 (3H,s,2'''-OCH$_3$), 3.60(3H,s,3'''-OCH$_3$), 4.20 (1H, d, J$_1$', 2', 8Hz,H$_1$'), 5.87 (1H,dq,J$_{13,22}$1.5 Hz, $_{13,14}$10.5 Hz, H$_{13}$), 6.22 (1H,d,J$_{10,11}$15.5 Hz, H$_{10}$), 7.29 (1H,d,J$_{10,11}$15.5 Hz,H$_{11}$) and 9.67 (1H,s,H$_{20}$).

D. 4"-O-Acetyl-b 20-deoxo-20-[(4,4-dioxothiomorpholinyl)imino]-tylosin

4"-O-Acetyltylosin (prepared as in part C of this Example) (500 mg.) and 1-N-amino -4,4-dioxothiomorpholine (78 mg.) are dissolved in dry dichloromethane (100 ml.) and the mixture stirred at 25° C. for 75 hours, The solution is evaporated to dryness. Chromatography of the residue on a silica gel column (30+5 cm.) using 25% acetone in hexane as the eluant gives 4"-O-acetyl-20-deoxo-20-[(4,4-dioxothiomorpholinyl)imino]-tylosin as a colourless, amorphous solid having Rotation: [α]D$^{26}$−64.5° (CHCl$_3$); UV:λ$_{max}$(CF$_3$CH$_2$OH) 230 nm (ε 7,453); 286 nm (ε22,306), IR:λ$_{max}$ (CDCl$_3$) 3510, 2990, 2950, 2900, 1735, 1690, 1600, 1320, 1250, 1195, 1175, 1133, 1055 cm.−$^1$; NMR:ε $_H$ (CDCl$_3$) 1.80 (3H,d,J$_{13,22}$ 1.5 Hz,22-CH$_3$), 2.17 (3H,s,4"-OCOCH$_3$), 2,54 (6H,s,3'-N(CH$_3$)$_2$), 3,50 (3H,s,2'''-OCH$_3$), 3.64 (3H,s,3'''-OCH$_3$), 5.95 (1H,dq, J$_{13,22}$1.5 Hz, J$_{13,14}$10 Hz, H$_{13}$), 6.30 (1H,d,J$_{10,11}$ 16 Hz,H$_{10}$), 7.00 (1H,t,J$_{19,20}$ 5 Hz, H$_{20}$) and 7.38 (1H,d,J$_{10,11}$ 16 Hz,H$_{11}$).

EXAMPLE 6

A. 2',4"-Di-O-acetyl-4'''-O-(tert-butyldimethylsilyl) 20-deoxo-20-[(4,4-dioxothiomorpholinyl)-imino)]-tylosin 4'''-O-(tert)-Butyldimethylsilyl)-20-deoxo-20-[(4,4-dioxothiomorpholinyl)-imino]-tylosin (prepared as in Parts A and B of Example 2) (1.16 g) is dissolved in dry pyridine (5 ml) and acetic anhydride (1 ml) is added. The mixture is stirrred at 25° C. for 20 hours. The solution is evaporated to dryness and the residue azeotroped with toluene. The residue is taken up in dichloromethane-water. The dichloromethane layer is washed successively with water and saturated brine, then dried (MgSO$_4$), filtered and evaporated to dryness to give 2',4''-di-O-acetyl-4'''-O-(tert-butyldimethylsilyl)-20-deoxo-20-[(4,4-dioxothiomorpholinyl)-imino]-tylosin, a colourless amorphous solid, having the following characteristics Rotation: [α]D$^{26}$-−56.3° (CHCl$_3$); UV: λ$_{max}$ (CF$_3$-CH$_2$OH) 234 nm (ε6,433), 286 nm (ε20,760); IR:-λ$_{max}$ (CDCl$_3$) 3510, 2975, 2950, 2900, 1740, 1685, 1595, 1317, 1240, 1175, 1130, 1050 cm.−$^1$; NMR: δ $_H$(CDCl$_3$) 0.12 (3H,s,4'''-SiCH$_3$), 0.15 (3H,s,4'''-SiCH$_3$), 0.93 (9H,s, 4'''-SiC(CH$_3$)$_3$), 1.80 (3H,d,J$_{13,22}$ 1.5 Hz, 22-CH$_3$), 2.10 (3H,s,2'-OCOCH$_3$), 2.18 (3H,s,4''-OCOCH$_3$), 2.44 (6H,s,3'-N(CH$_3$)$_2$), 3.52 (3H,s,2'''-OCH$_3$), 3.63 (3H,s,3'''-OCH$_3$), 6.00 (1H,dq,J$_{13,22}$ 1.5 Hz,J$_{13,14}$ 10 Hz,H$_{13}$), 6.32 (1H,d,J$_{10,11}$ 15 Hz,H$_{10}$), 7.00 (1H,t,J$_{19,20}$ 5 Hz,H$_{20}$) and 7.40 (1H,d,J$_{10,11}$ 15 Hz,H$_{11}$).

B.

2',4''-Di-O-acetyl-20-deoxo-20-[(4,4-dioxothiomorpholinyl)-imino]-tylosin

2',4''-Di-O-acetyl-4'''-O-(tert-butyldimethylsilyl)-20-deoxo-20-[(4,4-dioxothiomorpholinyl)-imino]-tylosin (prepared as in part A of this Example) (2.3 g) and anhydrous tetra-n-butylammonium fluoride (obtained by azeotroping the trihydrate (583 mg) with toluene) are dissolved in dry tetrahydrofuran (100 ml). the resulting solution is allowed to remain at 25° C. for 2 hours under dry argon gas. The solution is evaporated to dryness and the residue taken up in dichloromethane. The dichloromethane solution is washed with saturated aqueous sodium bicarbonate water, dried (MgSO$_4$), filtered and evaporated to dryness. Chromatography of the residue on a silica gel column (60×2 cm) using 40% acetone in hexane as the eluant gives 2',4''-di-O-acetyl-20-deoxo-20-[(4,4-dioxothiomorpholinyl)-imino]-tylosin as a colorless amorphous solid, having: Rotation: [α]D$^{26}$ −71.6° (CHCl$_3$); UV: λ$_{max}$ (CF$_3$CH$_2$OH) 232 nm (ε7,355), 286 nm (ε22,958); IR:ν$_{max}$ (CDCl$_3$) 3520, 2980, 2950, 2900, 1740, 1720, 1680, 1595, 1315, 1240, 1170, 1128, 1050 cm.−$^1$; NMR:δ$_H$(CDCl$_3$) 1.79 (3H, d, J$_{13,22}$ 1.5 Hz, 22-CH$_3$), 2.08 (3H, s, 2'-OCOCH$_3$), 2.17 (3H, s, 4''-OCOCH$_3$), 2.43 (6H, s, 3'-N(CH$_3$)$_2$), 3.50 (3H, s, 2'''-OCH$_3$), 3.63 (3H, s, 3'''-OCH$_3$), 5.96 (1H, dq, J$_{13,22}$ 1.5 Hz, J$_{13,14}$ 10 Hz, H$_{13}$), 6.12 (1H, d, J$_{10,11}$ 15.5 Hz, H$_{10}$), 7.00(1H,t, J$_{19,20}$ 5 Hz, H$_{20}$) and 7.40 (1H, d, J$_{10,11}$ 15.5 Hz, H$_{11}$).

C.

4''-O-Acetyl-20-deoxo-20-[(4,4-dioxothiomorpholinyl)-imino]-tylosin.

2',4''-Di-O-acetyl-20-dioxo-20-[(4,4-dioxothiomorpholinyl)-imino]-tylosin (prepared as in part B of this Example (1 g) is dissolved in methanol (80 ml) and the mixture is allowed to remain at 25° C. After 68 hours, triethylamine (1 ml) was added and the mixture is allowed to remain at 25° C. for a further 6 hours. The solution is evaporated to dryness and the resulting residue chromatographed on a silica gel column (30×5 cm) using 25% acetone in hexane as the eluant to give 4''-O-acetyl-20-deoxo-20-[(4,4-dioxothiomorpholinyl)-imino]-tylosin, identical to that prepared by parts A through D of Example 5.

EXAMPLE 7

A. 2'-O-Acetyl-4'''-O-(tert-butyldimethylsilyl)-3'', 4''-O-carbonyl -20-deoxo-20-[(4,4-dioxothiomorpholinyl)-imino]-tylosin.

2'-O-Acetyl-4'''-O-(tert-butyldimethylsilyl)-20-deoxy-20-[(4,4-dioxothiomorpholinyl)-imino]-tylosin (prepared as in parts A through C of Example 2) (1.2 g) is dissolved in dry dichloromethane (50 ml) and N,N'-carbonyldiimidazole (178 mg) is added. The mixture is stirred at 25° C. for 20 hours. The solution is evaporated to dryness and the residue chromatographed on a silica gel column (200 g) using 15% acetone in dichloromethane as the eluant to give 2'-O-acetyl-4'''-O-(tert-butyldimethylsilyl)-3'',4''-O-carbonyl-20-deoxo-20-[(4,4-dioxothiomorpholinyl)-imino]-tylosin as a colorless, amorphous solid, having Rotation: [α]$_D$$^{26}$ −46.3° (CHCl$_3$); UV:λ$_{max}$(CH$_3$OH) 283 nm (ε20,900); NMR:δ$_H$(CDCl$_3$) 0.10 (3H, s, 4'''-SiCH$_3$), 0.14 (3H, s, 4'''-Si CH$_3$), 0.93 (9H, s, 4'''-SiC(CH$_3$)$_3$), 1.52 (3H, s, 3''-CH$_3$), 1.77 (3H, d, J$_{13,22}$ 1.5 Hz, 22-CH$_3$), 2.00 (3H, s, 2'-OCOCH$_3$), 2.40 (6H, s, 3'-N(CH$_3$)$_2$), 3.48 (3H, s,2'''-OCH$_3$), 3.61 (3H, s, 3'''-OCH$_3$), 4.60 (1H, d, J$_{1'',2''}$ 8 Hz, H$_{1''}$), 5.91 (1H, dq, J$_{13,22}$ 1.5 Hz, J$_{13,14}$ 10 Hz, H$_{13}$) 6.24 (1H, d, J$_{10,11}$ 15 Hz, H$_{10}$), 6.94 (1H, t, J$_{19,20}$ 5 Hz, H$_{20}$) and 7.32 (1H, d, J$_{10,11}$ 15 Hz, H$_{11}$).

B.

2'-O-Acetyl-3'',4''-O-carbonyl-20-deoxo-20[(4,4-dioxothiomorpholinyl)-imino]-tylosin 2'-O-Acetyl-4'''-O-(tert-butyldimethylsilyl)-3'', 4''-O-carbonyl-20-deoxy-20-[(4,4-dioxothiomorpholinyl)-imino]-tylosin (prepared as in part A of this example) (1.05 g) is dissolved in anhydrous tetrahydrofuran (25 ml) and tetra-n-butylammonium fluoride trihydrate (0.32 g) is added. The mixture is stirred at 25° C. for 5 hours. The solution is evaporated to dryness and the residue taken up in dichloromethane-water. The dichloromethane layer is washed with water, dried (MgSO$_4$), filtered and evaporated to dryness. Chromatography of the residue on a silica gel column (100 g) using 75% acetone in dichloromethane gives 2'-O-acetyl-3'',4''-O-carbonyl-20-deoxo-20-[(4,4-dioxothiomorpholinyl)-imino]-tylosin as a colorless, amorphous solid, having Rotation: [α]$_D$$^{26}$ −54.7° (CHCl$_3$); UV:λ$_{max}$ (CH$_3$OH) 280 nm (ε11,100); NMR:δ$_H$ (CD$_3$COCD$_3$), 1.56 (3H, s, 3''-CH$_3$), 1.86 (3H, d, J$_{13,22}$ 1.5 Hz, 22-CH$_3$), 2.01 (3H,s,2'-OCOCH$_3$), 2.44 (6H, s, 3'-N(CH$_3$)$_2$), 3.47 (3H,s,2'''-OCH$_3$), 3.53 (3H,s,3'''-OCH$_3$), 5.90 (1H, dq, J$_{13,22}$ 1.5Hz, J$_{13,14}$ 10 Hz, H$_{13}$), 6.54 (1H, d, J$_{10,11}$ 15Hz, H$_{10}$), 7.04 (1H, t, J$_{19,20}$ 5 Hz, H$_{20}$) and 7.25 (1H, d, J$_{10,11}$ 15 Hz, H$_{11}$).

C. 3'', 4''-O-Carbonyl-20-deoxo-20-[(4,4-dioxothiomorpholinyl)-imino]-tylosin 2'-O-Acetyl-20-deoxo-3'',4''-O-carbonyl-20-[(4,4-dioxothiomorpholinyl)-imino]-tylosin (prepared as in part B of this example) (840 mg) is dissolved in methanol (100 ml) and the resultant solution allowed to remain at 25° C. for 72 hours. The solution is then evaporated to dryness and the residue chromatographed on a silica gel column (110×2.5 cm) using 30% acetone in hexane as the eluant to give 3'',4''-O-carbonyl-20-deoxo-20[(4,4-dioxothiomoropholinyl)-imino]-tylosin as a colorless, amorphous solid, having Rotation: [α]$_D$$^{26}$ −59.2° (CHCl₃); NMR: $\delta_H$(CD₃CPCD₃), 1.56 (3H,s, 3''-CH₃), 1.85 (3H, d, $J_{13,22}$ 1.5 Hz, 22-CH₃), 2.56 (6H, s, 3'-N(CH₃)₂), 3.48 (3H, s, 2'''-OCH₃), 3.56 (3H, s, 3'''-OCH₃), 4.32 (1H, d, $J_{1'2'}$ 8 Hz, H₁'), 4.59 (1H, d, $J_{1''',2'''}$ 8 Hz, H₁'''), 5.99 (1H, dq, $J_{13,22}$ 1.5 Hz, $J_{13,14}$ 10 Hz, H₁₃), 6.56 (1H, d, $J_{10,11}$ 16 Hz, H₁₀), 7.13 (1H, t, $J_{19,20}$ 5 Hz, H₂₀) and 7.32 (1H, d, $J_{10,11}$ 16 Hz, H₁₁).

EXAMPLE 8

Repetition of the procedure detailed in Example 4 utilizing the appropriate "1-amino reactant" affords the following compounds of this invention:
20-[(piperidyl)imino]-20-deoxo-4''-O-iso-valeryltylosin,
20-[(4-methylpiperidyl)imino]-20-deoxo-4''-O-iso-valeryltylosin,
20-[(4,4-ethylenedioxypiperidyl)imino]-20-deoxo-4''-O-iso-valeryltylosin,
20[(4-benzyloxypiperidyl)imino]-20-deoxo-4''-O-iso-valeryltylosin,
20-[(4-methoxypiperidyl)imino]-20-deoxo-4''-O-iso-valeryltylosin,
20-[(4-acetyloxypiperidyl)imino]-20-deoxo-4''-O-iso-valeryltylosin,
20-[(4-methyl-4-hydroxypiperidyl)imino]-20-deoxo-4''-O-iso-valeryltylosin,
20-[(4-ethyl-4-propionyloxypiperidyl)imino]-20-deoxo-4''-O-iso-valeryltylosin,
20-[(4-propyl-4-ethoxypiperidyl)imino]-20-deoxo-4''-O-iso-valeryltylosin,
20-[(4-phenethylpiperidyl)imino]-20-deoxo-4''-O-iso-valeryltylosin,
20-[(4-benzoyloxypiperidyl)imino]-20-deoxo-4''-O-iso-valeryltylosin,
20-[(4-butoxycarbonylpiperidyl)imino]-20-deoxo-4''-O-iso-valeryltylosin,
20-[(4-carboxypiperidyl)imino]-20-deoxo-4''-O-iso-valeryltylosin,
20-[(4-dimethylaminocarbonylpiperidyl)imino]-20-deoxo-4''-O-iso-valeryltylosin,
20-[(4-methylpiperazinyl)imino]-20-deoxo-4''-O-iso-valeryltylosin,
20-[(4-benzylpiperazinyl)imino]-20-deoxo-4''-O-iso-valeryltylosin,
20-[(4-phenethylpiperazinyl)imino]-20-deoxo-4''-O-iso-valeryltylosin,
20-[(morpholinyl)imino]-20-deoxo-4''-O-iso-valeryltylosin,
20-[(thiomorpholinyl)imino]-20-deoxo-4''-O-iso-valeryltylosin,
20-[(4-β-hydroxyethylpiperazinyl)imino]-20-deoxo-4''-O-iso-valeryltylosin,
20-[(4-carbamoylpiperidyl)imino]-20-deoxo-4''-O-iso-valeryltylosin,
20-[(pyrrolidyl)imino]-20-deoxo-4''-O-iso-valeryltylosin,
20-[(homopiperidyl)imino]-20-deoxo-4''-O-iso-valeryltylosin,
20-[(2,6-dimethylpiperidyl)imino]-20-deoxo-4''-O-iso-valeryltylosin,
20-[(4-oxo-2-thioxo-3-thiazolidinyl)imino]-20-deoxo-4''-O-iso-valeryltylosin,
20-[(2,4-dioxoimidazolidinyl)imino]-20-deoxo-4''-O-iso-valeryltylosin,
20-[(4-phenylpiperidyl)imino]-20-deoxo-4''-O-iso-valeryltylosin,
20-[(4-hydroxy-4-phenylpiperidyl)imino]-20-deoxo-4''-O-iso-valeryltylosin,
20-[(4-cyano-4-phenylpiperidinyl)imino]-20-deoxo-4''-O-iso-valeryltylosin,
20-[4-(p-chlorophenyl)-4-hydroxypiperidyl)imino-20-deoxo-4''-O-iso-valeryltylosin,
20-[4-(p-chlorophenyl)-b 3,4-dehydropiperidyl]imino-20-deoxo-4''-O-iso-valeryltylosin,
20-[4-(o-tolyl)piperazinyl]imino-20-deoxo-4''-O-iso-valeryltylosin,
20-[4-(m-tolyl)piperazinyl]imino-20-deoxo-4''-O-iso-valeryltylosin,
20-[4-(α,α,α trifluoro-m-toly)piperazinyl]-imino-20-deoxy-4''-O-iso-valeryltylosin,
20-[4-(benzyl)piperazinyl]imino-20-deoxo-4''-O-iso-valeryltylosin,
20-[4-(p-chlorobenzhydryl)piperazinyl]imino-20-deoxo-4''-O-iso-valeryltylosin,
20-[4-(phenyl)-3,4-dehydropiperidyl]imino-20-deoxo-4''-O-iso-valeryltylosin,
20-[(4-benzylpiperidyl)imino]-20-deoxo-4''-O-iso- valeryltylosin,
20-[(4-phenylpiperazinyl)imino]-20-deoxo-4''-O-iso-valeryltylosin,
20-[4-(p-fluorophenyl)piperazinyl]imino-20-deoxo-4''-O-iso-valeryltylosin,
20-[4-(o-chlorophenyl)piperazinyl]imino-20-deoxo-4''-O-iso-valerytylosin,
20-[4-(m-chlorophenyl)piperazinyl]imino-20-deoxo-4''-O-iso-valeryltylosin,
20-[4-(p-chlorophenyl)piperazinyl]imino-20-deoxo-4''-O-iso-valeryltylosin,
20-[4-(o-methoxyphenyl)piperazinyl]imino-20-deoxo-4''-O-iso-valeryltylosin,
20-[4-(p-methoxyphenyl)piperazinyl]imino-20-deoxo-4''-O-iso-valeryltylosin,
20-[4-(p-acetylphenyl)piperazinyl]imino-20-deoxo-4''-O-iso-valeryltylosin,

EXAMPLE 9

Substantial repetition of the procedures detailed in the foregoing Examples utilizing the appropriate starting materials and reagents affords the following compounds of the invention:
20-deoxo-20-[(4,4-dioxothiomorpholinyl)-imino]-4''-O-propionyltylosin,
20-deoxo-20-[(4,4-dioxothiomorpholinyl)-imino]-4''-O-butyryltylosin,
20-deoxo-20-[(4,4-dioxothiomorpholinyl)-imino]-4''-O-iso-butyryltylosin,
20-deoxo-20-[(4,4-dioxothiomorpholinyl)-imino]-4''-O-valeryltylosin,
20-deoxo-20-[(4,4-dioxothiomorpholinyl)-imino]-3''-O-acetyl-4''-O-iso-valeryltylosin,
20-deoxo-20-[(4,4-dioxothiomorpholinyl)-imino]-3''-O-acetyl-4''-O-valeryltylosin,
30-deoxo-20-[(4,4-dioxothiomorpholinyl)-imino]-3''-O-acetyl-4''-O-butyryltylosin,
20-deoxo-20-[(4,4-dioxothiomorpholinyl)-imino]-3''-O-acetyl-4''-O-propionyltylosin, and
20-deoxo-20-[(4,4-dioxothiomorpholinyl)-imino]-3''-O-propionyl-4''-O-butyryltylosin.

EXAMPLE 10

| Capsule | |
|---|---|
| 20-deoxo-20-[(4,4-dioxothiomorpholinyl)imino]-4''-O—iso-valeryltylosin | 250.00 mg. |
| Lactose | 248.75 mg. |

| -continued | |
|---|---|
| Capsule | |
| Magnesium Stearate | 1.25 mg. |
| | 500.00 mg. |

Procedure

1. Blend the antibacterial and the lactose.
2. Add the magnesium stearate and mix.
3. Fill capsule.

EXAMPLE 11

Oral Suspension (to give a dose of 125 mg/5 ml)

20-deoxo-20-[(4,4-dioxothiomorpholinyl)-imino]-4"-O-iso-valeryltylosin: 25.00 gms.
Magnesium Aluminum Silicate: 9.50 gms.
Sodium Carboxymethylcellulose U.S.P.: 2.50 gms.
Flavor: q.s.
Color: q.s.
Methylparaben, U.S.P.: 0.90 gms.
Propylparaben, U.S.P.: 0.20 gms.
Polysorbate 80, U.S.P.: 1.00 gms.
Sorbitol Solution, U.S.P.: 500.00 gms.
Water, q.s.: 1000.00 ml.

Procedure

1. Heat 200 ml. of water to boiling, and dissolve in it one half of the parabens. Cool to about 70° C., then mix in the Polysorbate 80. Sprinkle in the silicate, stirring until a uniform smooth suspension results. 2. Heat an additional 200 ml. of water to boiling, and dissolve in it the remainder of the parabens. Disperse the CMC in this until a smooth gel results. Mix in the Sorbitol Solution. Then dissolve the sodium citrate.

3. Add the product of Step 2 to that of Step 1 slowly, with constant stirring. Cool the mixture to 25° C. Add the 20-deoxo-20-[(4,4-dioxothiomorpholinyl)-minio]-4"-O-iso-valeryltylosin, tartrate flavor, and color mixing thoroughly. Add sufficient quantity of water to make the total volume 1000 ml.

EXAMPLE 12

| Topical Ointment | |
|---|---|
| 20-deoxo-20-[(4,4-dioxothiomorpholinyl)-imino]-4"-O—iso-valeryltylosin | 10 gms. |
| Petrolatum | 990 gms. |
| | 1000 gms. |

Procedure

1. Melt the petrolatum.
2. Slurry the antibacterial with about 10% of the petrolatum and pass through a colloid mill.
3. Mix the milled slurry with the remainder of the molten petrolatum. allow to cool.

EXAMPLE 13

Topical Cream 20-deoxo-20-[(4,4-dioxothiomorpholinyl)-imino]-4"-O-iso-valeryltylosin: 10 gms.
Stearic Acid: 200 gms.
Sorbitan Monostearate: 104 gms.
Sorbitan Monoleate: 20 gms.
Polyoxyethylene sorbitan Monolaurate: 56 gms.
Water, q.s.: 100 ml.

Procedure

1. Heat the stearic acid, sorbitan monostearate, sorbitan monoleate, and polyoxyethylene sorbitan monolaurate to 65° C.
2. Heat about 90% of the water to 70° C.
3. Add the water to Step 1 and mix to form a cream base.
4. Slurry the antibacterial with about 10% of the water and pass through a colloid mill.
5. Add the milled slurry to the molten base and mix. Allow to cool.

What is claimed is:

1. A compound of the formula

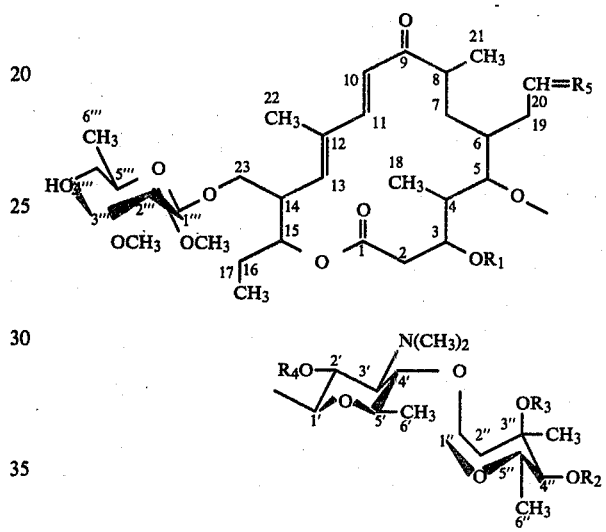

wherein
$R_1$ is hydrogen or an acyl group selected from alkanoyl of 2 to 5 carbon atoms, palmityl, stearyl, lauryl, oleyl, chloroacetyl, benzoyl, adamantanecarbonyl, cyclopropanecarbonyl, cyclohexanecarbonyl, β-cyclohexylpropionyl, phenylacetyl, phenoxyacetyl, mandelyl, 2-thienylacetyl, alkyl-, aryl- and aralkylsulfonyl, substituted aryl- and aralkylsulfonyl, wherein the substituents on the aryl portions are halogen, nitro and alkoxy groups, succinyl, maleyl, fumaryl, malonyl and phthalyl;
$R_2$ is acyl, wherein acyl is as defined in $R_1$;
$R_3$ is hydrogen or acyl, wherein acyl is as defined in $R_1$; or $R_2$ and $R_3$ are together a carbonyl group linking the 3"-and 4"-hydroxyl groups;
$R_4$ is hydrogen or acyl, wherein acyl is as defined in $R_1$;
$R_5$ is selected from the group consisting of

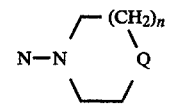

wherein
n is 0–2, and
Q is selected from the gorup consisting of $CH_2$, $CR_6R_7$, $CHR_6$, $CHR_7$, $NH, NR_6$, O, S, $SO_2$, CHOH, $CHOR_6$, $CHOR_7$,

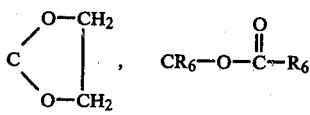

CHCOOH, CHCOOR$_6$, CHCONH$_2$, and CHCONR$_6$R$_7$, wherein R$_6$ and R$_7$ may be the same or different each being a member of the group consisting of (C$_1$-C$_6$)alkyl, (C$_7$-C$_{10}$)aralkyl and (C$_6$-C$_{10}$)aryl including X-substituted aryl and aralkyl, wherein X is halogen, trifluoromethyl, (C$_1$-C$_6$) alkoxy, or (C$_1$-C$_6$) alkylcarbonyl; N—NH—aralkyl, and

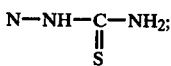

and the non-toxic pharmaceutically acceptable acid addition salts thereof.

2. A compound according to claim 1 wherein R$_5$ is a group of the formula

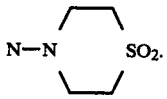

3. A compound according to claim 1 or 2 wherein R$_1$, R$_3$ and R$_4$ are hydrogen and R$_2$ is an acyl group selected from the group consisting of acetyl, propionyl, n-butyryl and iso-valeryl.

4. A compound according to claim 1 or 2 wherein R$_1$ is acetyl, R$_3$ and R$_4$ are hydrogen and R$_2$ is an acyl group selected from the group consisting of acetyl, propionyl, n-butyryl and iso-valeryl.

5. A compound according to claim 1 or 2 wherein R$_1$ and R$_3$ are hydrogen and R$_2$ and R$_4$ are acyl groups selected from the group consisting of acetyl, propionyl, n-butyryl and iso-valeryl.

6. A compound according to claim 1 or 2 wherein R$_1$ and R$_4$ are hydrogen, and R$_2$ and R$_3$ are acyl groups selected from the group consisting of acetyl, propionyl, n-butyryl and iso-valeryl.

7. A compound according to claim 1 or 2 wherein R$_1$ is hydrogen and R$_2$, R$_3$ and R$_4$ are acyl groups selected from the group consisting of acetyl, propionyl, n-butyryl and iso-valeryl.

8. A compound according to claim 1 or 2 wherein R$_2$ and R$_3$ are a bridging carbonyl group.

9. The compound according to claim 2 which is 20-deoxo-20-[(4,4-dioxothiomorpholinyl)imino]-4″-O-iso-valeryltylosin.

10. The compound according to claim 2 which is 4″-O-acetyl-20-deoxo-20-[(4,4-dioxothiomorpholinyl)-imino]tylosin.

11. A compound according to claim 2 which is 2′,4″-di-O-acetyl-20-deoxo-20-[(4,4-dioxothiomorpholinyl)-imino]tylosin.

12. A compound according to claim 2 which is 2′-O-acetyl-20-deoxo-20-[(4,4-dioxothiomorpholinyl)-imino]-4″-O-iso-valeryltylosin.

13. A compound according to claim 2 which is 4′-O-n-butyryl-20-deoxo-20[(4,4-dioxothiomorpholinyl)-imino]-3″-O-propionyltylosin.

14. A compound according to claim 2 which is 2′-O-acetyl-4″-O-n-butyryl-20-deoxo-20-[(4,4-dioxo-thiomorpholinyl)imino]-3″-O-propionyltylosin.

15. A compound according to claim 2 which is 3″-O-acetyl-20-deoxo-20-[(4,4-dioxothiomorphilinyl)-imino]-4″-O-iso-valeryltylosin.

16. A compound according to claim 2 which is 2′,3″-di-O-acetyl-20-deoxo-20-[(4,4-dioxothiomorpholinyl)-imino]-4″-O-iso-valeryltylosin.

17. A compound according to claim 2 which is 3″,4″-O-carbonyl-20-deoxo-20-[(4,4-dioxothiomorpholinyl)-imino]tylosin.

18. A compound according to claim 2 which is 2′-O-acetyl-3″,4″-O-carbonyl-20-deoxo-20-[(4,4-dioxothiomorpholinyl) imino]-tylosin.

19. 20-deoxo-20-[(4,4-dioxothiomorpholinyl)-imino]-tylosin.

20. A method of eliciting an antibactrial response in a mammal having a gram positive bacterial infection which comprises administering to the mammal a therapeutically effective quantity of a compound according to claim 1.

21. A method according to claim 20 wherein R$_5$ is

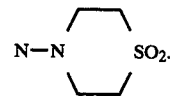

22. A method according to claim 21 wherein the compound utilized is 4″-O-acetyl-20-deoxo-20-[(4,4-dioxothiomorpholinyl)imino]tylosin.

23. A method according to claim 21 wherein the compound utilized is 20-deoxy-20-[(4,4-dioxothiomorpholinyl)-inino]4″-O-iso-valeryltylosin.

24. A method according to claim 21 wherein the compound utilized is 2′, 4″-di-O-acetyl-20-deoxo-20-[(4,4-dioxothiomorpholinyl)imino]tylosin.

25. A method according to claim 21 wherein the compoundutilized is 2′-O-acetyl-20-deoxo-20-[(4,4-dioxothiomorpholinyl)imino]-4″-O-iso-valeryltylosin.

26. A method according to claim 21 wherein the compound utilized is 4″-O-n-butyryl-20-deoxo-20-[(4,4-dioxothiomorpholinyl)imino]-3″-O-propionyltylosin.

27. A method according to claim 21 wherein the compound utilized is 2′-O-acetyl-4″-O-n-butyryl-20-deoxo-20-[(4,4-dioxothiomorpholinyl)imino]-3″-O-propionyltylosin.

28. A method according to claim 21 wherein the compound utilized is 3″-O-acetyl-20-deoxo-20-[(4,4-dioxothiomorpholinyl)imino]-4″-O-iso-valeryltylosin.

29. A method according to claim 21 wherein the compound utilized is 2′,3″-di-O-acetyl-20-deoxo-20-[(4,4-dioxothiomorpholinyl)imino]-4″-O-iso-valeryl-tylosin.

30. A method according to claim 21 wherein the compound utilized is 3″,4″-O-carbonyl-20-deoxo-20-[(4,4-dioxothiomorpholinyl)imino]-tylosin.

31. A method according to claim 21 wherein the compound utilized is 2′-O-acetyl-3″,4″-O-carbonyl-20-deoxo-20-[(4,4-dioxothiomorpholinyl)imino]-tylosin.

32. A pharmaceutical composition adapted for the treatment of a mammal having a gram positive bacterial infection which comprises a therapeutically effective quantity of a compound according to claim 1 or 2 in admixture with a pharmaceutically acceptable carrier therefor.

33. A pharmaceutical composition according to claim 32 which comprises 4''-O-acetyl-20-deoxo-20-[(4,4-dioxothiomorpholinyl)imino]-tylosin.

34. A pharmaceutical composition according to claim 32 which comprises 20-deoxo-20-[(4,4-dioxothiomorpholinyl)imino]-4''-O-iso-valeryltylosin.

35. A pharmaceutical composition according to claim 32 which comprises 2',4''-di-O-acetyl-20-deoxo-20-[(4,4-dioxothiomorpholinyl)imino]-tylosin.

36. A pharmaceutical composition according to claim 32 which comprises 2'-O-acetyl-20-deoxo-20-[(4,4-dioxothiomorpholinyl)imino]-4''-O-iso-valeryltylosin.

37. A pharmaceutical composition according to claim 32 which comprises 4''-O-n-butyryl-20-deoxo-20-[(4,4-dioxothiomorpholinyl)imino]-3''-O-propionyltylosin.

38. A pharmaceutical composition according to claim 32 which comprises 2'-O-acetyl-4''-O-n-butyryl-20-deoxo-20-[(4,4-dioxothiomorpholinyl)imino]-3''-O-propionyltylosin.

39. A pharmaceutical composition according to claim 32 which comprises 3''-O-acetyl-20-deoxo-20-[(4,4-dioxothiomorpholinyl)imino]-4''-O-iso-valeryltylosin.

40. A pharmaceutical composition according to claim 32 which comprises 2',3''-di-O-acetyl-20-deoxo-20-[(4,4-dioxothiomorpholinyl)imino]-4''-O-iso-valeryltylosin.

41. A pharmaceutical composition according to claim 32 which comprises 3'',4''-O-carbonyl-20-deoxo-20-[(4,4-dioxothiomorpholinyl)imino]-tylosin.

42. A pharmaceutical composition according to claim 32 which comprises 2'-O-acetyl-3'',4''-O-carbonyl-20-deoxo-20-[(4,4-dioxothiomorpholinyl)imino]-tylosin.

43. A pharmaceutical composition according to claim 32 adapted for oral administration.

44. A pharmaceutical composition according to claim 32 adapted for topical composition.

45. A pharmaceutical composition according to claim 32 adapted for injectable administration.

* * * * *